United States Patent
Coulson et al.

(10) Patent No.: US 10,285,750 B2
(45) Date of Patent: May 14, 2019

(54) SYSTEMS AND METHODS FOR OPERATING AN ELECTROSURGICAL GENERATOR

(71) Applicant: COVIDIEN LP, Mansfield, MA (US)

(72) Inventors: Rebecca J. Coulson, Lyons, CO (US); Gary M. Couture, Longmont, CO (US); Sara E. Anderson, Erie, CO (US); Prakash Manley, Lafayette, CO (US)

(73) Assignee: COVIDIEN LP, Manfield, MA (US)

( * ) Notice: Subject to any disclaimer, the term of this patent is extended or adjusted under 35 U.S.C. 154(b) by 93 days.

(21) Appl. No.: 14/255,051

(22) Filed: Apr. 17, 2014

(65) Prior Publication Data

US 2015/0032100 A1     Jan. 29, 2015

Related U.S. Application Data

(60) Provisional application No. 61/859,591, filed on Jul. 29, 2013.

(51) Int. Cl.
   *A61B 18/12*      (2006.01)
   *A61B 5/053*      (2006.01)
   (Continued)

(52) U.S. Cl.
   CPC ........ *A61B 18/1233* (2013.01); *A61B 5/0538* (2013.01); *A61B 18/1206* (2013.01);
   (Continued)

(58) Field of Classification Search
   CPC ............ A61B 18/1206; A61B 18/1233; A61B 2017/00154; A61B 2018/00601;
   (Continued)

(56) References Cited

U.S. PATENT DOCUMENTS 5,472,443 A    12/1995   Cordis et al.
5,558,671 A *   9/1996   Yates ............... A61B 17/07207
                                                                       606/34

(Continued)

FOREIGN PATENT DOCUMENTS

CN       1473024 A     2/2004
CN     101687213 A     3/2010

(Continued)

OTHER PUBLICATIONS

U.S. Appl. No. 14/297,812 dated Jun. 6, 2014, inventor: Wham.

(Continued)

*Primary Examiner* — Daniel W Fowler (57) ABSTRACT

The systems and methods according to embodiments of the present disclosure provide optimal tissue effect during an electrosurgical procedure. A system and method for controlling an electrosurgical generator is provided including sensing an impedance of target tissue; generating electrosurgical energy in a first phase at a first power level until the sensed impedance of the target tissue is greater than a first threshold impedance; generating a plurality of pulses of electrosurgical energy in a second phase at a second power level, each pulse being generated until the sensed impedance of the target tissue is greater than a second threshold impedance set for that pulse; and generating at least one high-voltage pulse in a third phase at a third power level for a predetermined duration to divide the target tissue.

14 Claims, 9 Drawing Sheets

(51) Int. Cl.
*A61B 17/00* (2006.01)
*A61B 18/00* (2006.01)

(52) U.S. Cl.
CPC ............... *A61B 2017/00154* (2013.01); *A61B 2018/00601* (2013.01); *A61B 2018/00678* (2013.01); *A61B 2018/00875* (2013.01)

(58) Field of Classification Search
CPC ........... A61B 2018/00678; A61B 2018/00875; A61B 5/0538
See application file for complete search history.

(56) References Cited

U.S. PATENT DOCUMENTS

| | | | |
|---|---|---|---|
| 5,709,680 A * | 1/1998 | Yates | A61B 17/07207 606/41 |
| 5,836,943 A * | 11/1998 | Miller, III | A61B 18/1206 606/34 |
| 6,080,149 A * | 6/2000 | Huang | A61B 18/1206 324/600 |
| 6,468,270 B1 | 10/2002 | Hovda et al. | |
| 6,837,888 B2 | 1/2005 | Ciarrocca et al. | |
| 6,942,660 B2 | 9/2005 | Pantera et al. | |
| 6,974,453 B2 | 12/2005 | Woloszko et al. | |
| D574,323 S | 8/2008 | Waaler | |
| 2002/0029036 A1 | 3/2002 | Goble et al. | |
| 2002/0143326 A1* | 10/2002 | Foley | A61B 18/1492 606/41 |
| 2002/0165531 A1* | 11/2002 | Goble | A61B 18/1445 606/40 |
| 2005/0203504 A1 | 9/2005 | Wham et al. | |
| 2006/0217707 A1* | 9/2006 | Daniel | A61B 18/1477 606/50 |
| 2007/0173804 A1* | 7/2007 | Wham | A61B 18/1206 606/34 |
| 2007/0173811 A1 | 7/2007 | Couture et al. | |
| 2007/0265616 A1* | 11/2007 | Couture | A61B 18/1442 606/48 |
| 2008/0188849 A1* | 8/2008 | Goldberg | A61B 18/1206 606/41 |
| 2008/0221565 A1* | 9/2008 | Eder | A61B 18/1206 606/40 |
| 2008/0287944 A1 | 11/2008 | Pearson et al. | |
| 2009/0240244 A1* | 9/2009 | Malis | A61B 18/1206 606/33 |
| 2011/0028963 A1 | 2/2011 | Gilbert | |
| 2011/0037484 A1 | 2/2011 | Gilbert | |
| 2011/0077630 A1 | 3/2011 | Tanaka et al. | |
| 2011/0208183 A1* | 8/2011 | Stockert | A61B 18/1206 606/35 |
| 2011/0238056 A1 | 9/2011 | Koss et al. | |
| 2012/0078139 A1* | 3/2012 | Aldridge | A61B 17/32009 601/2 |
| 2012/0179154 A1 | 7/2012 | Goldberg et al. | |
| 2014/0100559 A1 | 4/2014 | Wham et al. | |

FOREIGN PATENT DOCUMENTS

| | | |
|---|---|---|
| DE | 179607 C | 3/1905 |
| DE | 390937 C | 3/1924 |
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 10 2008058737 A1 | 4/2010 |
| EP | 0 246 350 A1 | 11/1987 |
| EP | 267403 A2 | 5/1988 |
| EP | 296777 A2 | 4/1989 |
| EP | 310431 A2 | 4/1989 |
| EP | 325456 A2 | 7/1989 |
| EP | 336742 A2 | 10/1989 |
| EP | 390937 A1 | 10/1990 |
| EP | 0 556 705 A1 | 8/1993 |
| EP | 608609 A2 | 8/1994 |
| EP | 0 836 868 A2 | 4/1998 |
| EP | 880220 A2 | 11/1998 |
| EP | 0 882 955 A1 | 12/1998 |
| EP | 1051948 A2 | 11/2000 |
| EP | 1366724 A1 | 12/2003 |
| EP | 1776929 A1 | 4/2007 |
| EP | 2111812 A2 | 10/2009 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| JP | 63 005876 A | 1/1988 |
| JP | 2002-065690 A | 3/2002 |
| JP | 2005040616 A | 2/2005 |
| JP | 2005-185657 A | 7/2005 |
| JP | 2007195981 A | 8/2007 |
| JP | 2010512181 A | 4/2010 |
| JP | 2011520520 A | 7/2011 |
| JP | 2013523219 A | 6/2013 |
| SU | 166452 | 11/1964 |
| SU | 727201 A2 | 4/1980 |
| WO | 02/11634 A1 | 2/2002 |
| WO | 02/45589 A2 | 6/2002 |
| WO | 03/090635 A1 | 11/2003 |
| WO | 06/050888 A1 | 5/2006 |
| WO | 08/053532 A1 | 5/2008 |
| WO | 2008071914 A2 | 6/2008 |
| WO | 2009146260 A1 | 12/2009 |

OTHER PUBLICATIONS

U.S. Appl. No. 14/297,890 dated Jun. 6, 2014, inventor: Wham.
U.S. Appl. No. 14/320,762 dated Jul. 1, 2014, inventor: Gilbert.
U.S. Appl. No. 14/320,804 dated Jul. 1, 2014, inventor: Gilbert.
Extended European Search Report for EP 14 17 7968 dated Oct. 13, 2014.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'", Neurosurgical Review 7:2-3 (1984) pp. 187-190.
Sugita et al., "Bipolar Coagulator with Automatic Thermocontrol", J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System", Innovations That Work; Company Newsletter; Sep. 1999.

(56) References Cited

OTHER PUBLICATIONS

"Electrosurgical Unit Analyzer ESU-2400 Series User Manual" Apr. 1, 2002; Retrieved from Internet: <URL:http://www.bcgroupintl.com/ESU_2400/Updates/ESU-2400_UM_Rev04.pdf>, pp. 6, 11, 73.
Ogden Goertzel Alternative to the Fourier Transform: Jun. 1993 pp. 485-487, Electronics World; Reed Business Publishing, Sutton, Surrey, BG vol. 99, No. 9. 1687.
Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.
Burdette et al. "In Vivo Probe Measurement Technique For Determining Dielectric Properties At VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator", 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al., "The Measurement of Physiologic Events by Electrical Impedence", Am. J. MI, Jan. Mar. 1964, pp. 16-27.
Cosman et al., "Methods of Making Nervous System Lesions", In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight And Absorbance Imaging Of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance", Applied Neurophysiology 51: (1988) pp. 230-242.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . ", Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297, Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System", 2 pp. Nov. 1995.
U.S. Appl. No. 10/406,690 dated Apr. 3, 2003 inventor: Behnke.
U.S. Appl. No. 10/573,713 dated Mar. 28, 2006 inventor: Wham.
U.S. Appl. No. 10/761,524 dated Jan. 21, 2004 inventor: Wham.
U.S. Appl. No. 11/242,458 dated Oct. 3, 2005 inventor: Becker.
U.S. Appl. No. 14/096,341 dated Dec. 4, 2013 inventor: Johnson.
U.S. Appl. No. 14/098,859 dated Dec. 6, 2013 inventor: Johnson.
U.S. Appl. No. 14/100,113 dated Dec. 9, 2013 inventor: Gilbert.
U.S. Appl. No. 14/147,294 dated Jan. 3, 2014 inventor: Gilbert.
U.S. Appl. No. 14/147,312 dated Jan. 3, 2014 inventor: Gilbert.
U.S. Appl. No. 14/168,296 dated Jan. 30, 2014, inventor: Mattmiller.
U.S. Appl. No. 14/174,551 dated Feb. 6, 2014 inventor: Johnson.
U.S. Appl. No. 14/174,607 dated Feb. 6, 2014 inventor: Friedrichs.
U.S. Appl. No. 14/179,724 dated Feb. 13, 2014 inventor: Johnson.
U.S. Appl. No. 14/180,965 dated Feb. 14, 2014 inventor: Larson.
U.S. Appl. No. 14/181,114 dated Feb. 14, 2014 inventor: Larson.
U.S. Appl. No. 14/182,797 dated Feb. 18, 2014 inventor: Wham.
U.S. Appl. No. 14/190,830 dated Feb. 26, 2014 inventor: Johnson.
U.S. Appl. No. 14/190,895 dated Feb. 26, 2014 inventor: Gilbert.
U.S. Appl. No. 14/255,051 dated Apr. 17, 2014 inventor: Coulson.
U.S. Appl. No. 14/262,219 dated Apr. 25, 2014, inventor: Gilbert.
U.S. Appl. No. 14/267,066 dated May 1, 2014, inventor: Friedrichs.
U.S. Appl. No. 14/268,187 dated May 2, 2014, inventor: Kerr.
U.S. Appl. No. 14/283,604 dated May 21, 2014, inventor: Behnke.
U.S. Appl. No. 14/297,771 dated Jun. 6, 2014, inventor: Wham.
Chinese Office Action dated Nov. 16, 2017 in corresponding Chinese Patent Application No. 201410340433.1 together with English translation, 14 pages.
Japanese Office Action dated May 17, 2018 in corresponding Japanese Patent Application No. 2014-152769 with English translation.
Australian Examination Report dated Aug. 7, 2018 in corresponding Australian Patent Application No. 2014203332.
Notice of Allowance issued by the Japanese Patent Office dated Feb. 1, 2019 in corresponding Japanese Patent Application No. 2014-152769, with English translation.

* cited by examiner

SYSTEMS AND METHODS FOR OPERATING AN ELECTROSURGICAL GENERATOR

CROSS REFERENCE TO RELATED APPLICATION

The present application claims the benefit of and priority to U.S. Provisional Application Ser. No. 61/859,591, filed on Jul. 29, 2013, the entire contents of which are incorporated herein by reference.

BACKGROUND

Technical Field

The present disclosure relates to systems and methods for operating an electrosurgical generator. More particularly, the present disclosure relates to a systems and methods for controlling the output of the electrosurgical generator for optimized cutting of tissue.

Background of Related Art

Electrosurgery involves application of high radio frequency electrical current to a surgical site to cut, ablate, or coagulate tissue. In monopolar electrosurgery, a source or active electrode delivers alternating current from the electrosurgical generator to the targeted tissue and a return electrode conducts the alternating current back to the generator. A patient return electrode is placed remotely from the active electrode to conduct the current back to the generator.

In bipolar electrosurgery return and active electrodes are placed in close proximity to each other such that an electrical circuit is formed between the two electrodes (e.g., in the case of an electrosurgical forceps). In this manner, the applied alternating current is limited to the body tissue positioned between the electrodes. Accordingly, bipolar electrosurgery generally involves the use of instruments where it is desired to achieve a focused delivery of electrosurgical energy between two electrodes positioned on the instrument, e.g., forceps or the like. A forceps is a pliers-like instrument which relies on mechanical action between its jaws to grasp, clamp, and constrict vessels or tissue. Electrosurgical forceps (open or endoscopic) utilize mechanical clamping action and electrical energy to effect hemostasis on the clamped tissue. The forceps include electrosurgical conductive surfaces which apply the electrosurgical energy to the clamped tissue. By controlling the intensity, frequency, and duration of the electrosurgical energy applied through the conductive plates to the tissue, the surgeon can coagulate, seal, and/or cut tissue. However, the above example is for illustrative purposes only and there are many other known bipolar electrosurgical instruments which are within the scope of the present disclosure.

SUMMARY

The systems and methods according to embodiments of the present disclosure provide optimal tissue effect during an electrosurgical procedure. According to one embodiment, the present disclosure provides for a method for controlling an electrosurgical generator.

In accordance with aspects of the present disclosure, a method for controlling an electrosurgical generator is provided including sensing an impedance of target tissue; generating electrosurgical energy in a first phase at a first power level until the sensed impedance of the target tissue is greater than a first threshold impedance; generating a plurality of pulses of electrosurgical energy in a second phase at a second power level, each pulse being generated until the sensed impedance of the target tissue is greater than a second threshold impedance set for that pulse; and generating at least one high-voltage pulse in a third phase at a third power level for a predetermined duration to divide the target tissue.

In some aspects of the present disclosure, the method further includes generating electrosurgical energy in an impedance sense phase at a fourth power level to sense an initial tissue impedance of the target tissue.

In some aspects of the present disclosure, the first threshold impedance is equal to a predetermined impedance rise amount above the initial tissue impedance.

In some aspects of the present disclosure, the second threshold impedance is equal to an adjustable impedance rise amount above the initial tissue impedance.

In some aspects of the present disclosure, the adjustable impedance rise amount at least one of increases, decreases, and remains the same for each successive pulse based on an adjustment factor.

In some aspects of the present disclosure, the adjustable impedance rise amount is multiplied by the adjustment factor for each successive pulse.

In some aspects of the present disclosure, the pulses in the second phase are applied until the sensed tissue impedance is greater than a maximum threshold impedance value.

In some aspects of the present disclosure, the method further includes determining a tissue type of the target tissue based on the sensed initial impedance of the target tissue; and generating a number of high-voltage pulses during the third phase based on the determined tissue type.

In some aspects of the present disclosure, if the sensed initial impedance of the target tissue is less than a tissue type threshold impedance value, the tissue type is determined to be a low impedance tissue type and the number of high-voltage pulses delivered during the third phase is set to a first value, and if the sensed initial impedance of the target tissue is greater than or equal to the tissue type threshold impedance value, the tissue type is determined to be a high impedance tissue type and the number of high-voltage pulses generated during the third phase is set to a second value, the second value being greater than the first value.

In some aspects of the present disclosure, the method further includes stopping the generation of at least one high-voltage pulse during the third phase if the sensed impedance of the target tissue exceeds a maximum threshold impedance value.

In some aspects of the present disclosure, the method further includes stopping the generation of at least one high-voltage pulse during the third phase if a phase difference between the voltage and current of the at least one high-voltage pulse is greater than a predetermined phase difference value.

In some aspects of the present disclosure, the generator is set to an off state having a fifth power level after each pulse of the plurality of pulses in the second phase for a predetermined duration, the predetermined duration being set such that the target tissue at least partially re-hydrates after each pulse of the plurality of pulses.

In some aspects of the present disclosure, the generator is set to an off state having a fifth power level after each pulse of the at least one high-voltage pulse in the third phase for a pre-determined duration, the pre-determined duration being set such that the target tissue at least partially re-hydrates after each pulse.

In some aspects of the present disclosure, the generator is set to an off state having a fifth power level after each pulse generated in the first, second, and third phases, each off state having a pre-determined duration.

In some aspects of the present disclosure, the method further includes generating, in the third phase, electrosurgical energy at the fourth power level before the at least one high-voltage pulse to sense the impedance of the target tissue and prepare the generator for a rapid rise in power to the third power level.

In some aspects of the present disclosure, the method further includes generating, in the third phase, electrosurgical energy at the fourth power level after that at least one high-voltage pulse to sense the impedance of the target tissue.

In accordance with aspects of the present disclosure, an electrosurgical generator is provided including an RF output stage coupled to a power source, a sensor configured to measure an impedance of the target tissue; and a controller configured to control the RF output. The RF output stage is configured to generate electrosurgical energy from power provided by the power source for delivery to target tissue. The controller is configured to control the RF output stage to: generate electrosurgical energy in a first phase at a first power level until the sensed impedance of the target tissue is greater than a first threshold impedance; generate a plurality of pulses of electrosurgical energy in a second phase at a second power level, each pulse of the plurality of pulses being generated until the sensed impedance of the target tissue is greater than a second threshold impedance set for that pulse; and generate at least one high-voltage pulse in a third phase at a third power level for a predetermined duration to divide the target tissue.

In some aspects of the present disclosure, the first threshold impedance is equal to a predetermined impedance rise amount above an initial tissue impedance measured by the sensor.

In some aspects of the present disclosure, the second threshold impedance is equal to an adjustable impedance rise amount above an initial tissue impedance measured by the sensor.

In some aspects of the present disclosure, the adjustable impedance rise amount at least one of increases, decreases, and remains the same for each successive pulse based on an adjustment factor, the adjustable impedance rise amount being multiplied by the adjustment factor for each successive pulse.

In accordance with aspects of the present disclosure, a method for treating target tissue is provided including delivering electrosurgical energy to the target tissue in a first phase at a first power level until a sensed tissue impedance of the target tissue is greater than a threshold target impedance; delivering a plurality of pulses of electrosurgical energy to the target tissue in a second phase at a second power level, each pulse being delivered until the sensed tissue impedance of the target tissue is greater than a threshold target impedance set for that pulse; and delivering at least one high voltage pulse to the target tissue in a third phase at a third power level for a pre-determined duration to divide the target tissue.

In accordance with aspects of the present disclosure, a method for controlling an electrosurgical generator is provided including sensing an impedance of target tissue; generating electrosurgical energy in an impedance sense phase at an initial power level for a first duration to sense an initial tissue impedance of the target tissue; generating electrosurgical energy in a first phase at a first power level until the sensed impedance of the target tissue is greater than a first threshold impedance; and generating a plurality of pulses of electrosurgical energy in a second phase at a second power level, each pulse being generated until the sensed impedance of the target tissue is greater than a second threshold impedance set for that pulse.

In some aspects of the present disclosure, the initial power level and the first duration are set so that the generated electrosurgical energy has little effect on the target tissue.

Any of the above aspects and embodiments of the present disclosure may be combined without departing from the scope of the present disclosure.

BRIEF DESCRIPTION OF THE DRAWINGS

Various embodiments of the present disclosure are described herein with reference to the drawings wherein.

DETAILED DESCRIPTION

Particular embodiments of the present disclosure are described below with reference to the accompanying drawings. In the following description, well-known functions or constructions are not described in detail to avoid obscuring the present disclosure in unnecessary detail.

The present disclosure provides for a system and method for cutting tissue. The method may be implemented as computer-readable instructions executed by a controller, e.g., a microcontroller, of the electrosurgical generator. The generator includes an RF output stage configured to supply electrosurgical energy to tissue via at least one active electrode configured to apply electrosurgical energy to tissue, sensing circuitry configured to measure impedance of tissue, and the controller. The generator according to the present disclosure can perform monopolar and/or bipolar electrosurgical procedures, including, for example, cutting, coagulation, ablation, and vessel sealing procedures.

The generator may include a plurality of outputs for interfacing with various electrosurgical instruments (e.g., a monopolar instrument, return electrode, bipolar electrosurgical forceps, footswitch, etc.). Further, the generator includes electronic circuitry configured to generate radio frequency energy specifically suited for various electrosurgical modes (e.g., cut, blend, coagulate, division with hemostasis, fulgurate, spray, etc.) and procedures (e.g., monopolar, bipolar, vessel sealing, etc.). In embodiments, the generator may be embedded, integrated, or otherwise coupled to the electrosurgical instruments providing for an all-in-one electrosurgical apparatus.

The systems and methods of the present disclosure provide for optimal tissue effect in an electrosurgical cutting procedure. The method is performed over the following operational phases: (1) initialize the tissue effect, (2) localize heat in the target tissue through impedance-based pulsing, and (3) separate tissue with focused energy density. In the first phase, power is delivered to the target tissue until the tissue impedance rises above a threshold. Then energy delivery is paused for an intermediate off state to allow for tissue rehydration. The purpose of the first phase is to get the target tissue cooking, but not to over-desiccate the target tissue before any significant energy delivery.

Prior to the first phase, the method may also include a fourth phase in which a small amount of power is delivered to the target tissue to sense the initial impedance of the target tissue. The sensed initial impedance of the target tissue is used to determine the current state of the instrument (e.g., to confirm that the instrument is not in an open circuit state) and to stabilize the sensor readings.

In the second phase, the power output from the generator is pulsed at a constant rate to steadily raise the tissue impedance. This pulsing preconditions the tissue in the cut zone of the target tissue to ensure a narrow band of desiccation for the third phase. In embodiments, the second phase does not over-desiccate the tissue prior to the third phase.

In the third phase, one or more high-voltage pulses are delivered for a prescribed amount or time. These pulses deliver the final burst of energy needed to divide the tissue in the cut zone of the target tissue. The third phase incorporates intelligent impedance-based pulsing to ensure tissue separation. It has been found that lower impedance tissues (e.g., isolated veins, porcine uterine mesometrium, etc.) typically only need one high-voltage pulse to divide the target tissue, while higher-impedance tissues (e.g., thin tissue, fatty mesentery, etc.) need two or more pulses to completely divide the target tissue. Thus, in the third phase, pulses are continually generated and delivered to the target tissue until a predetermined number of pulses have been generated or the tissue reaches a threshold impedance indicating that the tissue has already been divided. This enables a more intelligent shut-off of the cutting algorithm and ensures a complete cut.

Figure 1:
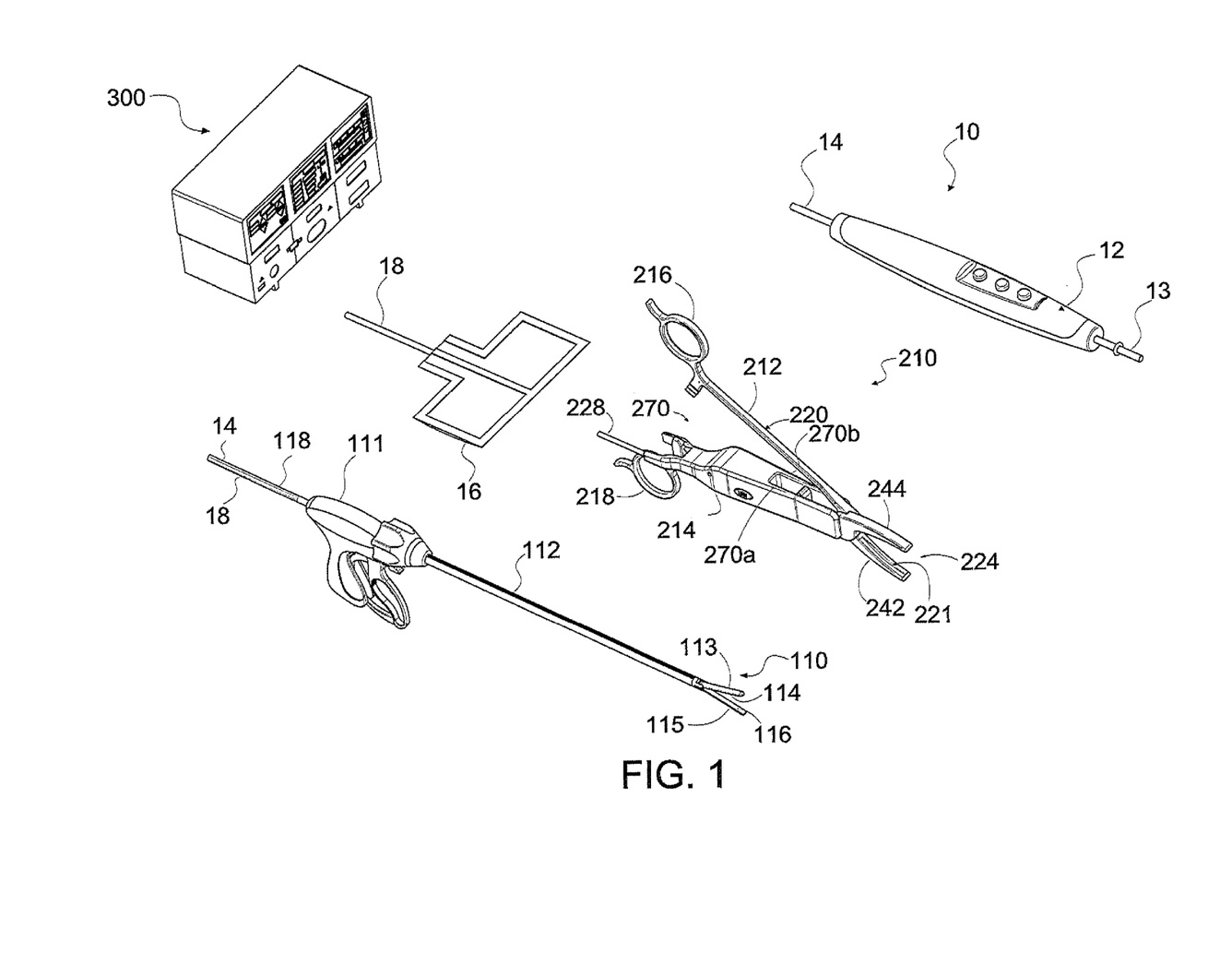
FIG. 1 is a perspective view of an electrosurgical generator and other components of an electrosurgical system according to embodiments of the present disclosure.

FIG. 1 is an illustration of a monopolar and bipolar electrosurgical system 10 according to the present disclosure. The system 10 may include one or more monopolar electrosurgical instruments 12 having one or more active electrodes 13 (e.g., electrosurgical cutting probe, ablation electrodes, etc.) for treating tissue of a patient. Electrosurgical alternating current is supplied to the instrument 12 by a generator 300 via a supply line 14 that is connected to an active terminal 230 (FIG. 3) of the generator 300, allowing the instrument 12 to cut, coagulate, ablate, and/or otherwise treat tissue. The alternating current is returned to the generator 300 through a return electrode pad 16 via a return line 18 at a return terminal 332 (FIG. 3) of the generator 300. For monopolar operation, the system 10 may include a plurality of return electrode pads 16 that, in use, are disposed on a patient to minimize the chances of tissue damage by maximizing the overall contact area with the patient. In addition, the generator 300 and the return electrode pads 16 may be configured for monitoring so-called "tissue-to-patient" contact to insure that sufficient contact exists therebetween to further minimize chances of tissue damage.

The system 10 may also include one or more bipolar electrosurgical instruments, for example, a bipolar electrosurgical forceps 110 or a bipolar electrosurgical forceps 310 having one or more electrodes for treating tissue of a patient. The bipolar electrosurgical instruments may be used with open and/or laparoscopic surgical procedures.

Figure 3:
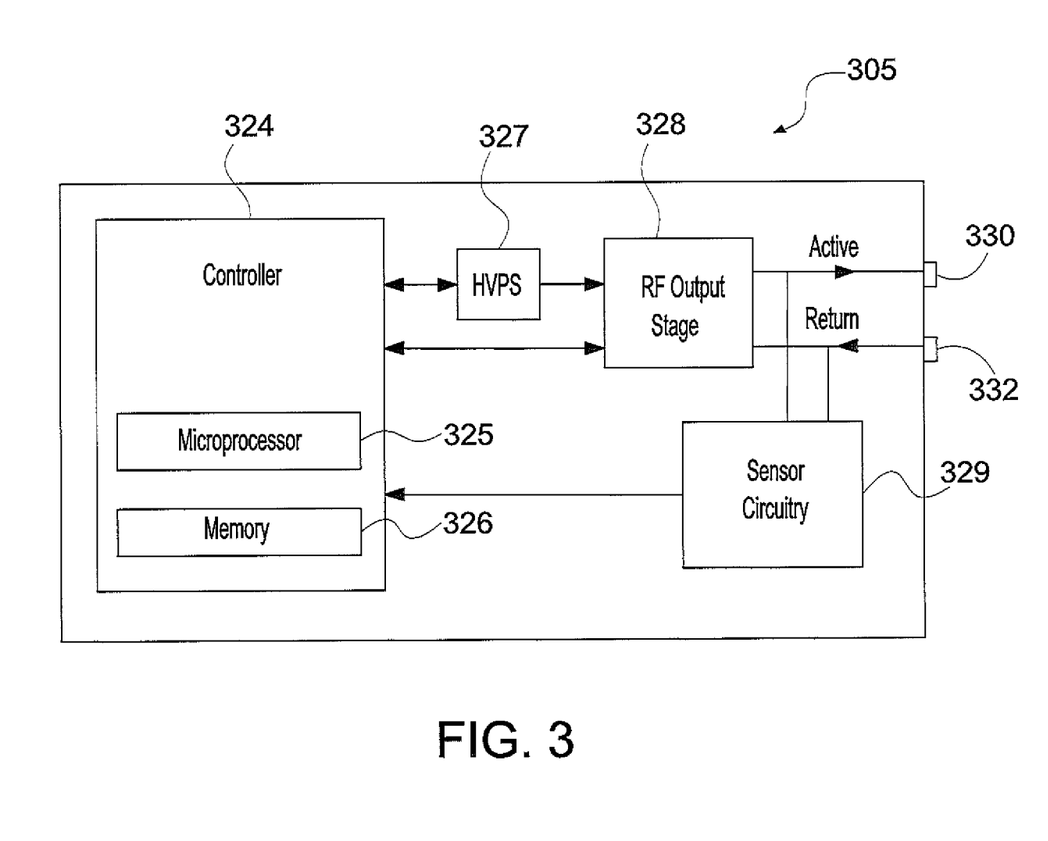
FIG. 3 is a block diagram of the generator circuitry of the electrosurgical generator of FIG. 2.

The bipolar electrosurgical forceps 110 includes a housing 111 and opposing jaw members 113 and 115 disposed at a distal end of a shaft 112. The jaw members 113 and 115 have one or more active electrodes 114 and a return electrode 116 disposed therein, respectively. The active electrode 114 and the return electrode 116 are connected to the generator 300 through cable 118 that includes the supply and return lines 14, 18 coupled to the active and return terminals 330, 332, respectively (FIG. 3). The electrosurgical forceps 110 is coupled to the generator 300 at a connector having connections to the active and return terminals 330 and 332 (e.g., pins) via a plug disposed at the end of the cable 118, wherein the plug includes contacts from the supply and return lines 14, 18 as described in more detail below.

The bipolar electrosurgical forceps 210 includes a mechanical forceps 220 having an end effector 224 and a disposable electrode assembly 221. Mechanical forceps 220 includes first and second elongated shaft members 212 and 214. Disposed at the proximal end portions of shaft members 212, 214 are handle members 216 and 218, respectively, that are configured to allow a user to effect movement of at least one of the shaft members 212 and 214 relative to the other. The end effector 224 includes opposing jaw members 242, 244 that extend from the distal end portions of shaft members 212 and 214, respectively. The jaw members 242, 244 are movable relative to each other in response to movement of shaft members 212, 214. A housing 270 having a pair of housing halves 270a, 270b is configured to matingly engage and releasably encompass at least a portion of shaft member 214. Forceps 210 includes an electrical cable 228 extending from housing 270 configured to electrically connect forceps 210 to a source of electrosurgical energy, such as electrosurgical generator 300, as shown in FIG. 1.

Figure 2:
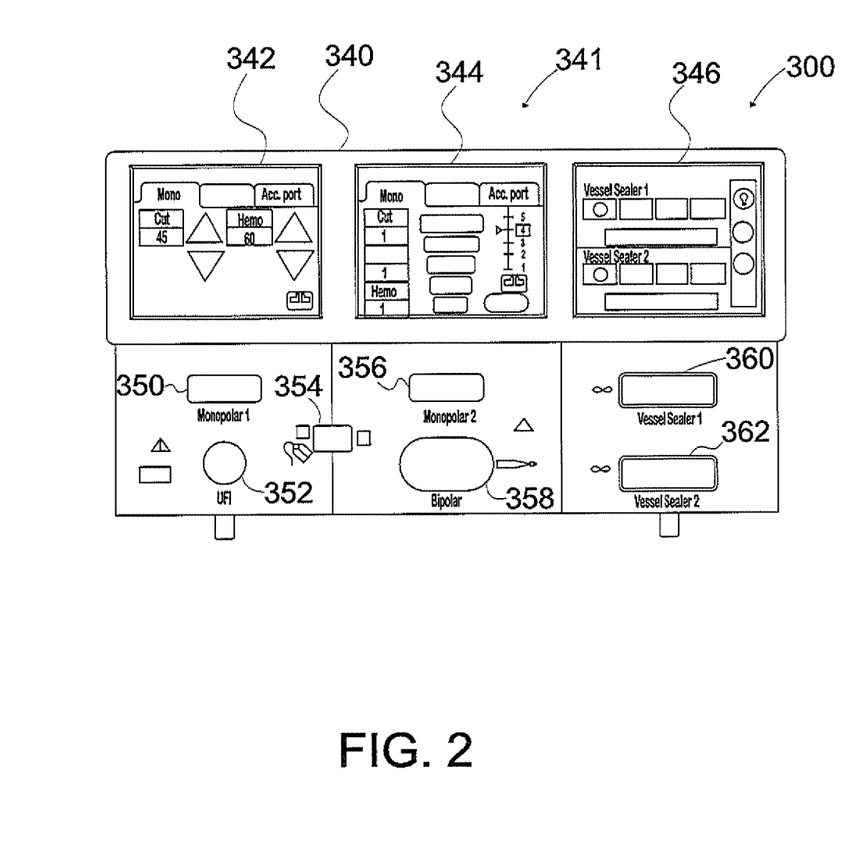
FIG. 2 is a front view of the electrosurgical generator of FIG. 1.

With reference to FIG. 2, a front face 340 of the generator 300 is shown. The generator 300 may be any suitable type (e.g., electrosurgical, microwave, etc.) and may include a plurality of connectors 350-362 to accommodate various types of electrosurgical instruments (e.g., electrosurgical instrument 12, electrosurgical forceps 110, electrosurgical forceps 210, etc.).

The generator 300 includes a user interface 341 having one or more display screens or information panels 342, 344, 346 for providing the user with a variety of output information (e.g., intensity settings, treatment complete indicators, etc.). Each of the display screens 342, 344, 346 is associated with a corresponding connector 350-362. The generator 300 includes suitable input controls (e.g., buttons, activators, switches, touch screen, etc.) for controlling the generator 300. The display screens 342, 344, 346 are also configured as touch screens that display a corresponding menu for the electrosurgical instruments (e.g., electrosurgical instrument 12, electrosurgical forceps 110, electrosurgical forceps 210, etc.). The user then adjusts inputs by simply touching corresponding menu options.

Display screen 342 controls monopolar output and the devices connected to the connectors 350 and 352. Connector 350 is configured to couple to a monopolar electrosurgical instrument (e.g., electrosurgical instrument 12) and connector 352 is configured to couple to a foot switch (not shown).

The foot switch provides for additional inputs (e.g., replicating inputs of the generator 300). Display screen 344 controls monopolar and bipolar output and the devices connected to the connectors 356 and 358. Connector 356 is configured to couple to other monopolar instruments. Connector 358 is configured to couple to a bipolar instrument.

Display screen 346 controls bipolar sealing procedures performed by the forceps 110 or forceps 210 that may be plugged into the connectors 360 and 362. The generator 300 outputs energy through the connectors 360 and 362 suitable for sealing tissue grasped by the forceps 110 or 210. In particular, display screen 346 outputs a user interface that allows the user to input a user-defined intensity setting. The user-defined intensity setting may be any setting that allows the user to adjust one or more energy delivery parameters, such as power, current, voltage, energy, etc. or sealing parameters, such as energy rate limiters, sealing duration, etc. The user-defined setting is transmitted to the controller 324 where the setting may be saved in memory 326. In embodiments, the intensity setting may be a number scale, such as for example, from one to ten or one to five. In embodiments, the intensity setting may be associated with an output curve of the generator 300. The intensity settings may be specific for each forceps 110 or 210 being utilized, such that various instruments provide the user with a specific intensity scale corresponding to the forceps 110 or 210.

FIG. 3 shows a block diagram of generator circuitry 305 of the generator 300 of FIG. 1 having a controller 324, a high voltage DC power supply 327 ("HVPS"), an RF output stage 328, and sensor circuitry 329. The HVPS 327 is connected to an AC source (e.g., electrical wall outlet) and provides high voltage DC power to an RF output stage 328, which then converts high voltage DC power into RF energy (e.g., an AC signal) and delivers the RF energy to the active terminal 330. The energy is returned thereto via the return terminal 332. In particular, the RF output stage 328 generates sinusoidal or rectangular waveforms of RF energy. The RF output stage 328 is configured to generate a plurality of waveforms having various duty cycles, peak voltages, waveform crest factors, and other suitable parameters. Certain types of waveforms are suitable for specific electrosurgical modes. For instance, the RF output stage 328 typically generates a 100% duty cycle sinusoidal waveform in cut mode, which is well-suited for ablating, fusing, and dissecting tissue, and a 1-25% duty cycle waveform in coagulation mode, which is suitable for cauterizing tissue to stop bleeding.

The controller 324 includes a processor 325 operably connected to a memory 326, which may include volatile memory (e.g., RAM) and/or non-volatile memory (e.g., flash media, disk media, etc.). The processor 325 includes an output port that is operably connected to the HVPS 327 and/or RF output stage 328 allowing the processor 325 to control the output of the generator 300 according to either open and/or closed control loop schemes. A closed loop control scheme is a feedback control loop in which the sensor circuitry 329 provides feedback to controller 324 (i.e., information obtained from one or more sensors for sensing various tissue parameters such as tissue impedance, fluid presence, output current, and/or voltage, etc.), and providing feedback to the controller 324. The controller 324 then signals the HVPS 327 and/or RF output stage 328 to adjust the DC and/or RF power supply, respectively. Those skilled in the art will appreciate that the processor 325 may be substituted by using any logic processor (e.g., control circuit) adapted to perform the calculations and/or set of instructions described herein including, but not limited to, a field programmable gate array, a digital signal processor, or combinations of these logic processors.

The processor 325 is coupled to the user interface 341 and is configured to modify modes, energy settings, and other parameters of the generator 300 in response to user input. The generator 300 is configured to operate in a variety of modes. In one embodiment, the generator 300 may generate an output according to the following modes: cut, blend, coagulate, division with hemostasis, fulgurate, spray, combinations of these modes, and the like. Each mode operates based on a pre-programmed power curve that controls the amount of power that is output by the generator 300 at varying impedances of the load (e.g., the target tissue). Each power curve includes power, voltage, and current control ranges that are defined by the user-selected power setting and the measured impedance of the load.

Referring now to FIGS. 4-9, the controller 324 of the generator 300 performs an optimized cutting algorithm for controlling the delivery of electrosurgical energy during a cutting procedure. The optimized cutting algorithm is configured to generate electrosurgical energy to target tissue in four phases, namely, impedance sense (IS), S1, S2 and S3, to effectively separate or divide the target tissue. The generator settings for each phase will now be described in further detail. In some instances, the generator 300 will be set to an "off" or low power state to allow the target tissue to re-hydrate to lower the impedance of the target tissue after the application of electrosurgical energy. In the "off" state, the output of the electrosurgical generator 300 is set to a power level P0 having a value from about 0 W to about 5 W and is typically set as close to 0 W as possible. In some embodiments, P0 is set slightly above 0 W to provide a trickle of electrosurgical energy and provide enhanced system stability for a generator supplying electrosurgical energy at 0 W.

Figure 4:
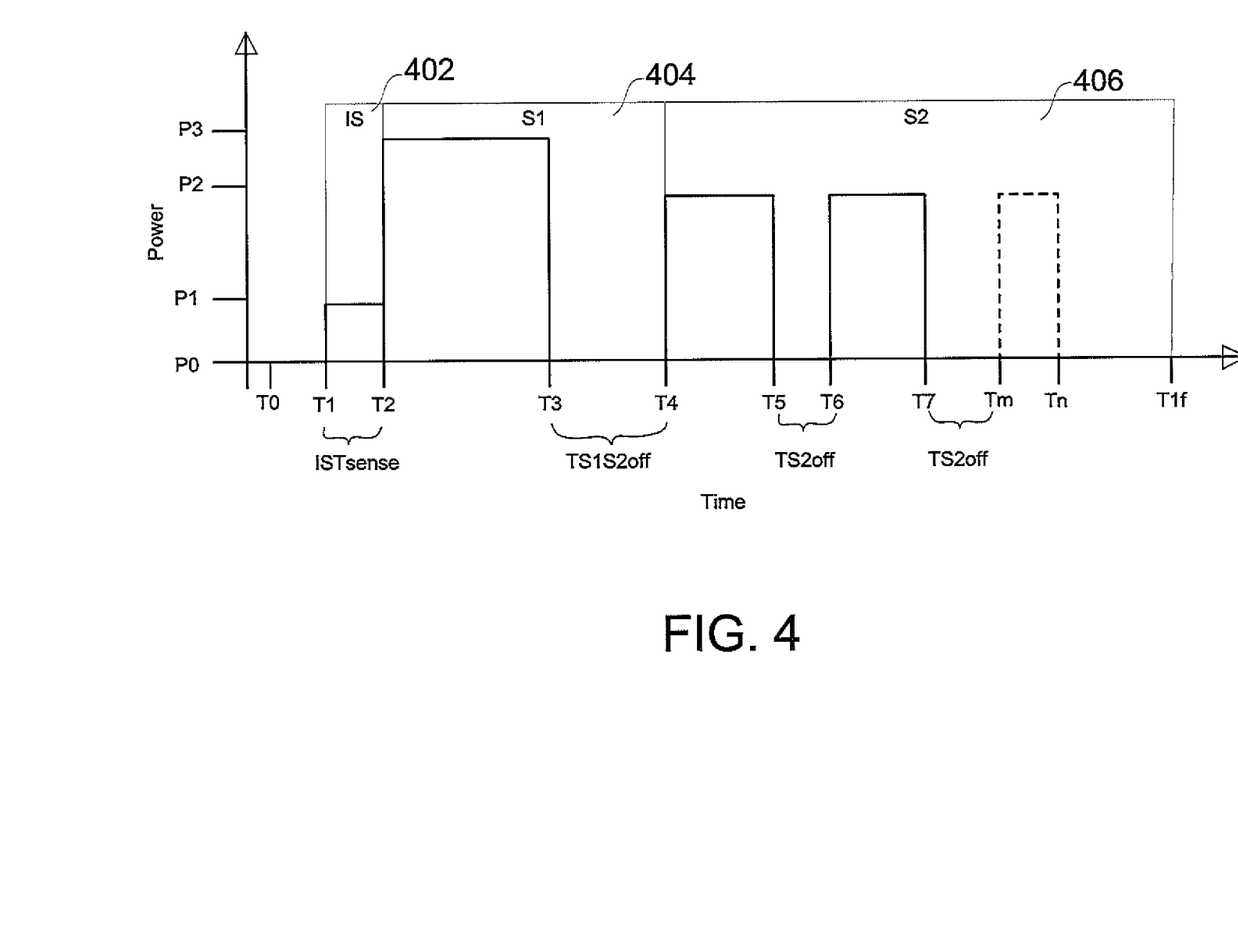
FIG. 4 is a graphical diagram illustrating the output power profile of the electrosurgical energy generated by the generator circuitry of FIG. 3 as a function of time for three phases according to an embodiment of the present disclosure.
Figure 5:
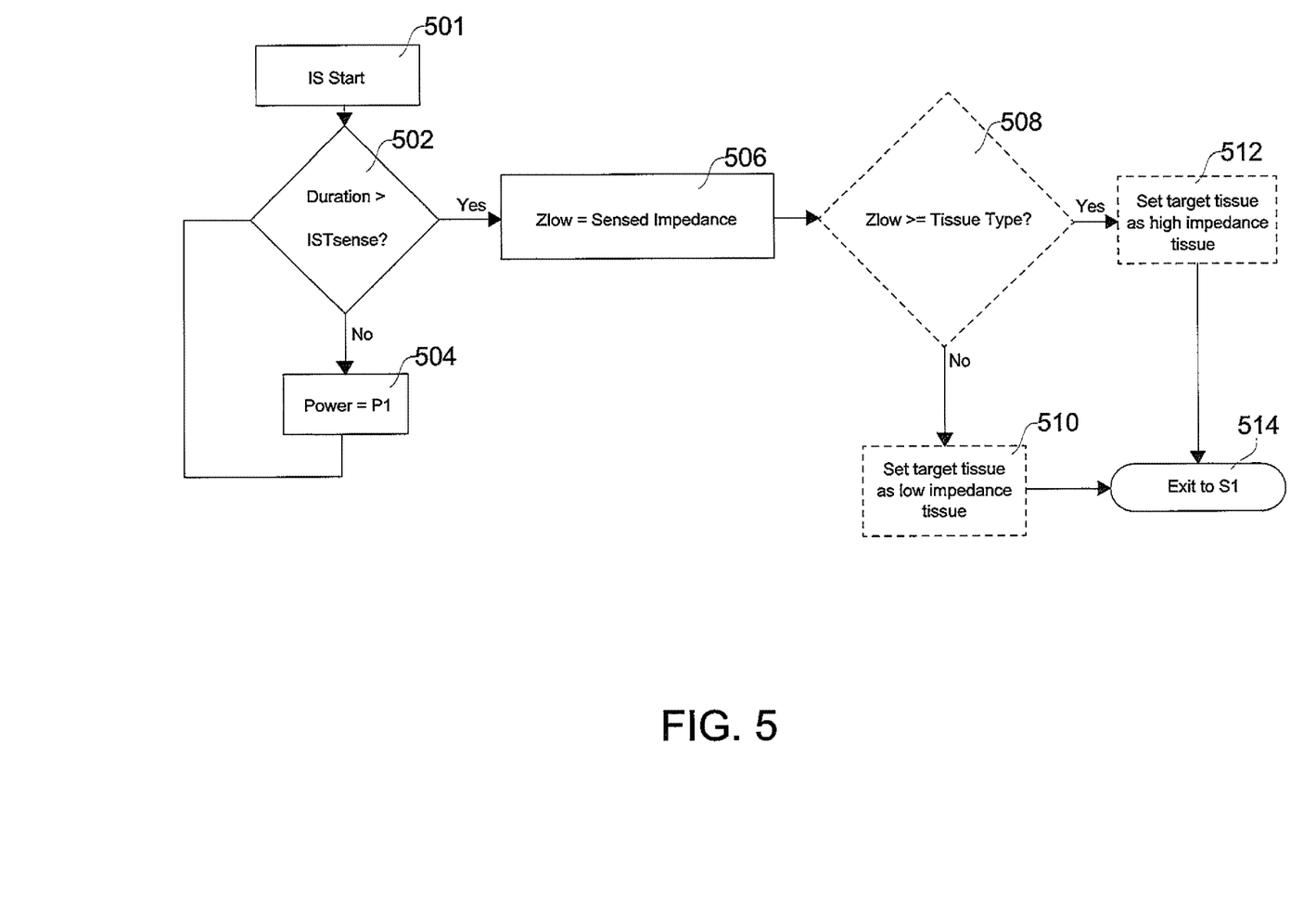
FIGS. 5-7 are flowcharts illustrating a method of controlling the power output from the generator circuitry during different operational phases according to embodiments of the present disclosure.

Referring now to FIGS. 4 and 5, after the IS phase 402 starts in step 501, the electrosurgical generator generates electrosurgical energy, which is output to the electrosurgical instrument and delivered to the target tissue by the electrosurgical instrument, at a constant power level P1 (step 504) for a set duration ISTsense (step 502) to allow the controller 324 of the generator circuitry 305 of FIG. 3 to determine initial parameters of the target tissue, for example, an initial tissue impedance Zlow. As shown in FIG. 5, if it is determined in step 502 that the duration is greater than the set duration ISTsense, then Zlow is set equal to the sensed impedance at that time in step 506. Power level P1 is typically set to a power level from about 0 W to about 5 W and, in some embodiments, is set to 5 W. The duration ISTsense is typically set from about 10 ms to about 500 ms and, in some embodiments, is set to 100 ms to provide sufficient time for the sensor readings to stabilize. No appreciable changing of the tissue occurs during the application of electrosurgical energy to the target tissue during the IS phase.

By applying electrosurgical energy to tissue at power level P1 for a duration ISTsense, the generator 300 can determine whether the electrosurgical instrument is in an "open" state based on a comparison of the sensed initial tissue impedance Zlow to an upper threshold value Zsensehigh. For example, an upper threshold value Zsensehigh of about 500Ω to about 2000Ω or more could be set for indicating that the instrument is in the "open" state, such as when there is no tissue disposed between the jaws of the instrument. In some embodiments, the upper threshold value Zsensehigh may be set to 1500Ω.

In some embodiments, the type of tissue may optionally be determined during the IS phase by comparing the initial tissue impedance Zlow to a threshold tissue impedance value TissueType, which is used to classify the target tissue as a low impedance tissue or a high impedance tissue. For example, when the initial tissue impedance Zlow is determined to be smaller than the threshold tissue impedance value TissueType (i.e., the initial tissue impedance Zlow is determined not to be greater than or equal to the threshold tissue impedance value TissueType) in step 508, the target tissue is set as a low impedance tissue in step 510. The low impedance tissue may require only one or two high-voltage pulses to divide tissue. On the other hand, when the initial tissue impedance Zlow is determined to be greater than or equal to the threshold tissue impedance value TissueType in step 508, the target tissue is set as a high impedance tissue in step 512. The high impedance tissue may require two or more high-voltage pulses for dividing the tissue. After the type of the tissue has been determined and set, the IS phase ends and the process exits the IS phase and proceeds to the first phase S1 in step 514.

Figure 6:
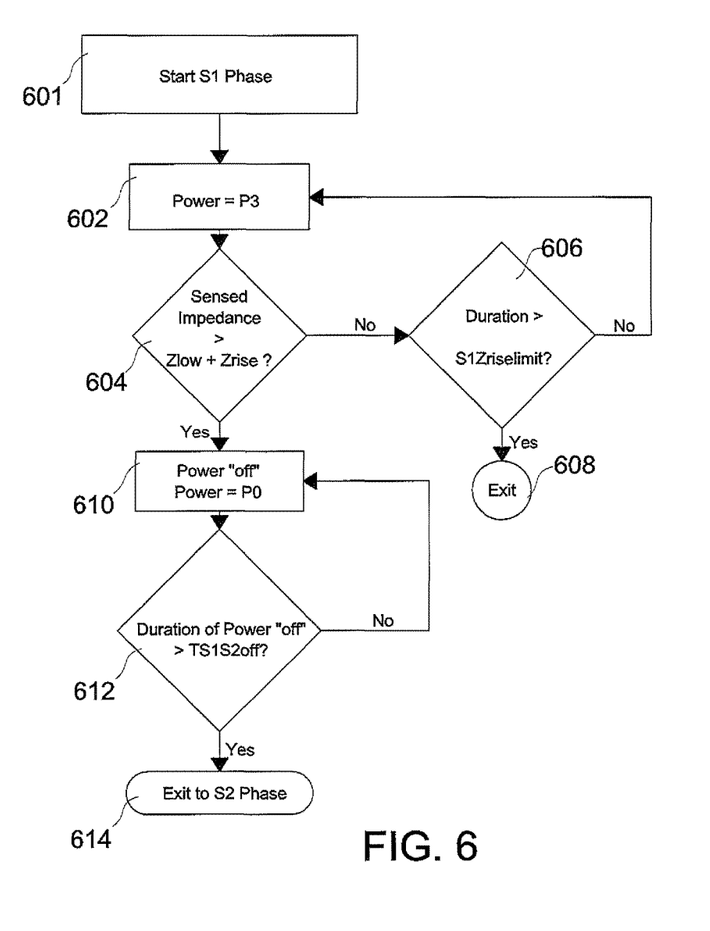

Referring now to FIGS. 4 and 6, during the S phase 404 or pre-cooking phase, which starts in step 601, the electrosurgical generator 300 generates electrosurgical energy at a constant power level P3 in step 602 until it is determined in step 604 that the tissue impedance increases from the sensed initial impedance Zlow by a threshold impedance rise amount Zrise, i.e., until it is determined that the tissue impedance is greater than Zlow+Zrise, to prepare the tissue for cutting. Power level P3 is typically set to a power value from about 10 W to about 100 W and, in some embodiments, is set to 40 W. Zrise is typically set to an impedance value from about 5Ω to about 100Ω and, in some embodiments, is set to 40Ω. The electrosurgical energy is generated and applied to the target tissue at the power level P3 until the impedance of the target tissue has increased from the sensed initial impedance Zlow by Zrise to reach a threshold impedance value of Zlow+Zrise.

Once it is determined in step 604 that the sensed impedance of the target tissue has reached Zlow+Zrise, the tissue has been pre-heated and the generator 300 is set to the "off" state to reduce or stop delivery of the electrosurgical energy to the target tissue by setting the power to power level P0 in step 610. The generator 300 is set to the "off" state for a duration TS1S2off before proceeding to the S2 phase 406 (steps 612 and 614). Setting the generator 300 to the "off" state before proceeding to the S2 phase 406 allows the target tissue to re-hydrate and reduces the impedance of the target tissue. TS1S2off is typically set to a duration from about 5 ms to about 1000 ms and, in some embodiments, to 50 ms.

If it is determined in step 606 that the sensed impedance of the target tissue does not reach Zlow+Zrise within a time S1ZriseLimit, the output from the electrosurgical generator 300 is shut off and the cutting algorithm is stopped in step 608 due to a lack of tissue response to the application of electrosurgical energy. S1ZriseLimit is typically set from about 0 ms to about 12000 ms and, in some embodiments, is set to 4000 ms.

Figure 7:
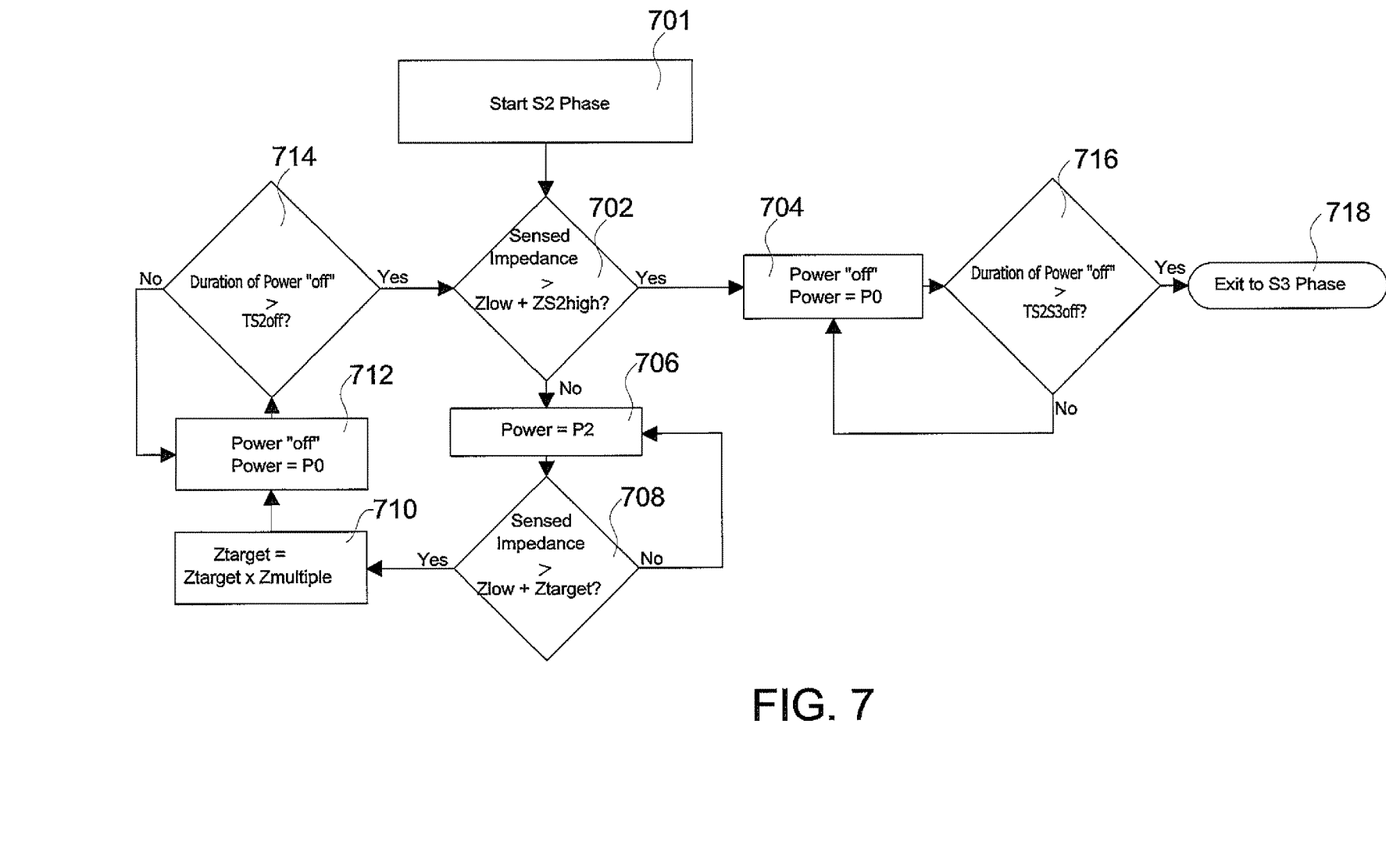

Referring now to FIGS. 4 and 7, during the S2 phase 406, which starts in step 701, the electrosurgical generator 300 generates multiple pulses of electrosurgical energy at a constant power level P2 in step 706 to prepare the target tissue for cutting. Power level P2 is typically set to a power value from about 10 W to about 200 W and, in some embodiments, is set to 20 W. After each pulse, the output of the electrosurgical generator 300 is set to the "off" state having the power level P0 in step 712 for a fixed duration TS2off as determined in step 714 to allow the target tissue to at least partially re-hydrate. TS2off is typically set to a duration from about 5 ms to about 1000 ms and, in some embodiments, is set to 50 ms.

Each pulse has a variable duration based on a comparison in step 708 of a sensed impedance of the target tissue to a target impedance threshold, which is equal to a target impedance rise amount Ztarget above Zlow for the current pulse. When it is determined in step 708 that the sensed impedance of the target tissue is greater than Ztarget+Zlow, the target impedance Ztarget for each successive pulse is adjusted by a multiplication factor Zmultiplier in step 710 such that each successive pulse drives the target tissue to a new target impedance. In some embodiments, the target impedance Ztarget for each successive pulse at least one of increases, decreases, or remains the same.

Ztarget is typically initialized to an impedance value from about 5Ω to about 1000Ω and, in some embodiments, Ztarget is initialized to 50Ω. The multiplier Zmultiplier is typically set to a value of about 1.01 to about 10.0 and in some embodiments is set to 1.2. The multiplier Zmultiplier may be adjusted to increase or decrease the number of pulses in the S2 phase 406 and to increase or decrease the amount of time that the target tissue is cooked during each pulse. In some embodiments, the multiplier Zmultiplier may alternatively be set to a value that is less than or equal to 1.00 to either maintain or decrease the target impedance Ztarget for each pulse. The electrosurgical generator 300 continues to generate pulses in the S2 phase 406 until the sensed tissue impedance reaches a threshold value ZS2high above the initial tissue impedance Zlow. ZS2high is typically set from about 50Ω to about 1000Ω and, in some embodiments, is set to 100Ω.

Figure 8:
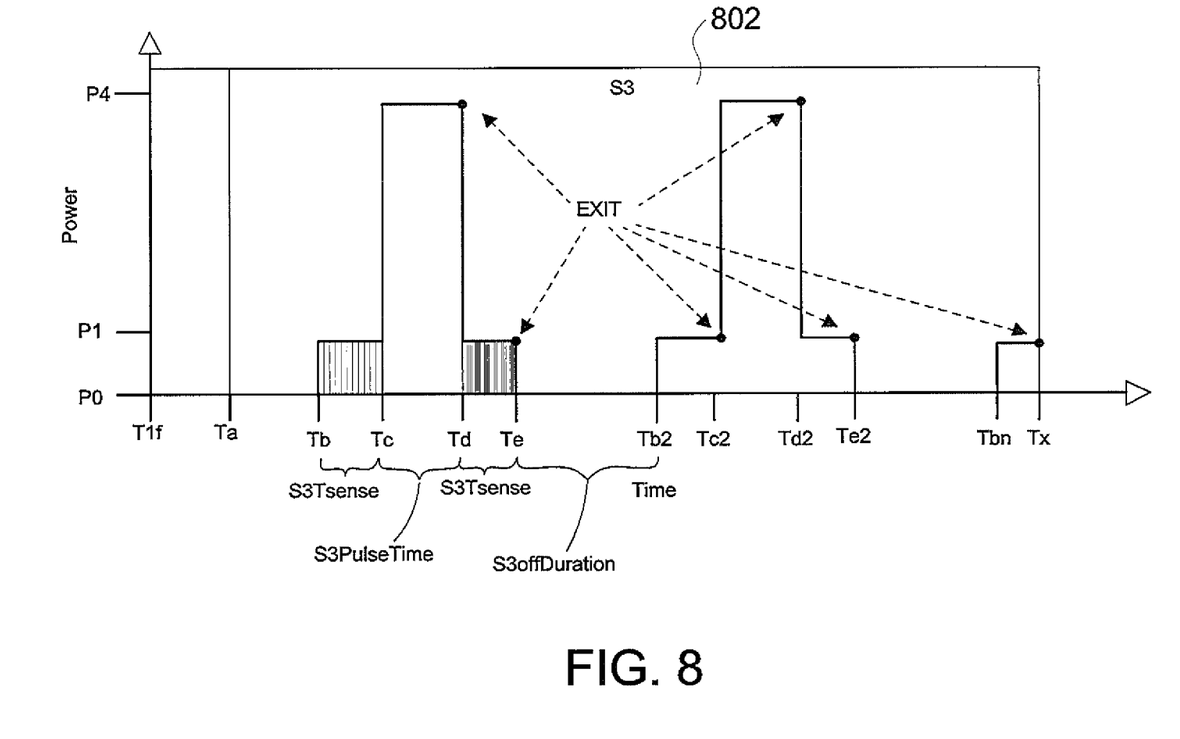
FIG. 8 is a graphical diagram illustrating the output power profile of the electrosurgical energy generated by the generator circuitry of FIG. 3 as a function of time for another phase according to an embodiment of the present disclosure.

The S2 phase 406 prepares the tissue for the final cutting by sequentially increasing the impedance of the target tissue in the cut zone to ensure a narrow band of desiccation for the final S3 phase 802. Near the end of the S2 phase 406, the generator is set to the power "off" state and the power level is set to power level P0 in step 704 for a duration TS2S3off determined in step 716 to allow the target tissue to re-hydrate and reduce impedance before proceeding to the S3 phase 802 in step 718. TS2S3off is typically set to a duration from about 5 ms to about 500 ms and, in some embodiments, is set to 100 ms.

Figure 9:
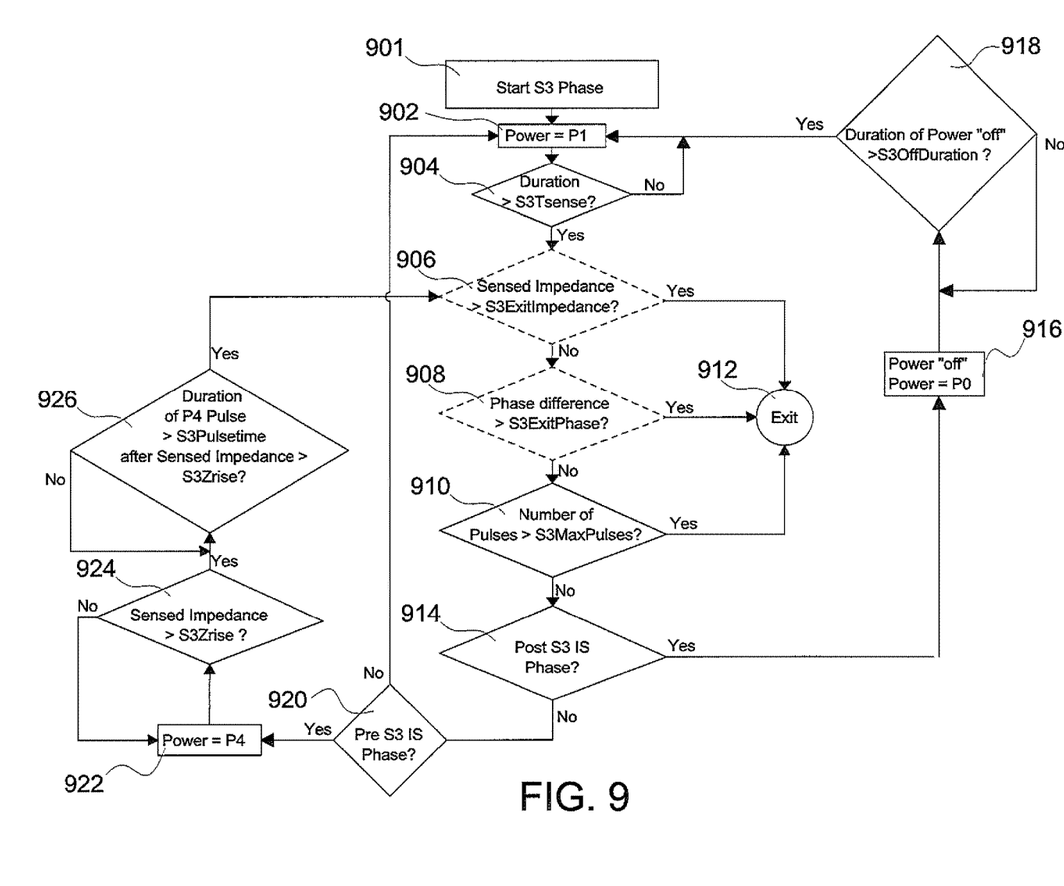
FIG. 9 is a flowchart illustrating a method of controlling the power output from the generator circuitry during another phase according to embodiments of the present disclosure.

Referring now to FIGS. 8 and 9, during the S3 phase 802, which starts in step 901, the electrosurgical generator 300 generates a high-voltage pulse of electrosurgical energy at a voltage level V1 and at a power level P4 in step 922 for a set duration S3Pulsetime determined in step 926 to divide the target tissue. Voltage level V1 for the high-voltage pulse of electrosurgical energy is typically set to a voltage from about 50 V to about 500 V. Power level P4 for the high-voltage pulse of electrosurgical energy is typically set to a power level from about 50 W to about 500 W and, in some embodiments, is set to 300 W.

The duration S3Pulsetime of the high voltage pulse is typically set to a value from about 5 ms to about 500 ms and, in some embodiments, is set to 10 ms. In some embodiments, the duration S3Pulsetime of the high voltage pulse is determined in step 926 after it is determined that the sensed impedance of the target tissue reaches a threshold minimum tissue impedance value S3Zrise in step 924. The threshold minimum tissue impedance value S3Zrise is typically set from about 500Ω to about 3000Ω and, in some embodiments, is set to 1500Ω. The high-voltage pulse at power level P4 during the S3 phase 802 is limited in duration to a maximum timeout value S3Pulsetime. If the sensed tissue impedance during the S3 high-voltage pulse does not reach the S3Zrise within a pre-determined time period S3PulseTime as determined in steps 924 and 926, the generator 300 shuts off the generation of electrosurgical energy.

In some procedures, two or more high-voltage pulses may be needed to divide the target tissue. The maximum number of high-voltage pulses S3MaxPulses to be delivered to the target tissue may be based on a predefined setting in the generator or based on an operator setting set by the clinician performing the procedure. For example, lower impedance tissues, such as isolated veins, porcine uterine mesometrium, etc., typically need only one high-voltage pulse to divide the target tissue, while higher impedance tissues, such as thin tissue, fatty mesentery, etc., may require two or more high-voltage pulses to completely divide the target tissue.

As described above with respect to FIG. 5, the type of tissue may be determined during the IS phase 402 by comparing the initial tissue impedance Zlow to a threshold tissue impedance value TissueType, which is used to classify the target tissue as a low impedance tissue or a high impedance tissue. For example, when the initial tissue impedance Zlow is smaller than the threshold tissue impedance value TissueType, the target tissue is set as a low impedance tissue requiring only one or two high-voltage pulses for dividing the tissue. When the initial tissue impedance Zlow is greater than or equal to the threshold tissue impedance value TissueType, the target tissue is set as a high impedance tissue requiring two or more high-voltage pulses for dividing the tissue. In some embodiments, S3MaxPulses is set to three pulses. The threshold tissue impedance value TissueType can be set to an impedance value from about 25Ω to about 500Ω and, in some embodiments, is set to 100Ω. The voltage level V1 for the high-voltage pulse may be adjusted based on the determined tissue type. For example, when the target tissue is determined to be a low impedance tissue, voltage level V1 may be set to 300 V and when the target tissue is determined to be a high impedance tissue, voltage level V1 may be set to 400 V.

When the S3 phase 802 includes more than one high-voltage pulse, the generator is set to power level P0 after each high-voltage pulse for a duration S3offDuration to allow the target tissue to re-hydrate and reduce the tissue impedance for successive high voltage pulses. By halting the supply of high-voltage energy to the target tissue between high-voltage pulses, optimized cutting of the target tissue can be achieved while minimizing the impact on surrounding tissue. The duration S3offDuration can be set to a duration from about 10 ms to about 2000 ms and, in some embodiments, is set to 1000 ms.

In some embodiments, the number of high-voltage pulses of electrosurgical energy delivered to the target tissue may be controlled by the generator based on sensed tissue and/or instrument properties. For example, during the S3 phase 802, the electrosurgical generator 300 may continue to generate high-voltage pulses to the target tissue at the power level P4 until either a predetermined number of high-voltage pulses are generated as determined in step 910, the target tissue reaches a predefined impedance threshold S3ExitImpedance as determined in step 906, or the phase difference between the voltage and the current of the electrosurgical energy generated by the electrosurgical generator 300 exceeds a threshold phase difference S3ExitPhase as determined in step 908. The predefined impedance threshold S3ExitImpedance is typically set to an impedance value from about 500Ω to about 5000Ω and, in some embodiments, is set to 2600Ω. The threshold phase difference S3ExitPhase is typically set to a phase shift from about 0.78 radians to about 1.56 radians and, in some embodiments, is set to 1.56 radians.

In some embodiments, the S3 phase 802 may include a pre-S3 impedance sense (IS) phase prior to each high-voltage pulse that is similar to the IS phase 402. If it is determined that the S3 phase 802 includes the pre-S3 IS phase 402 in step 920, the electrosurgical generator 300 initially generates electrosurgical energy before each high-voltage pulse at power level P1 in step 902 for the duration S3Tsense as determined in step 904 to help stabilize the sensor readings from sensor circuitry 329 before ramping up to the high voltage pulse at the power level P4 in step 922. The duration S3Tsense is typically set from about 10 ms to about 500 ms and, in some embodiments, is set to 100 ms to provide sufficient time for the sensor readings to stabilize. Applying electrosurgical energy at the power level P1 instead of the power level P0 before each high-voltage pulse was also found to be more favorable during testing for allowing the generator to achieve a rapid rise in power during the high-voltage pulse.

During the pre-S3 IS phase 402, the tissue and/or instrument properties are sensed to determine if any threshold exit conditions, such as the S3ExitImpedance, S3ExitPhase, or the pre-determined number of pulses have been met in steps 906, 908, and 910, respectively. In some embodiments, the pre-S3 IS phase 402 before the first S3 pulse does not check for exit conditions such that at least one high-voltage pulse is always delivered to the target tissue to divide the target tissue.

In some embodiments, the S3 phase 802 may also or alternatively include a post-S3 impedance sense (IS) phase after each high-voltage pulse. The electrosurgical generator 300 ramps down from the high-voltage pulse at the power level P4 to deliver electrosurgical energy at the power level P1 for a duration S3Tsense to allow the sensor circuitry 329 to stabilize. The post-S3 IS phase 402 allows the sensor circuitry 329 to monitor the delayed impedance effect after the high-voltage pulse has completed. This allows sufficient time for the impedance to rise after the high-voltage pulse before checking for the threshold exit conditions, such as the S3ExitImpedance, the S3ExitPhase, or the number of pulses, in steps 906, 908, and 910, respectively.

Once one of the exit conditions in steps 906, 908, or 910 has been met, the tissue is determined to have been divided and the method ends in step 912. In step 912, the generator 300 may also be deactivated or set to the power level P0. If none of the exit conditions have been met, it is determined whether the process has entered the post-S3 IS phase 402 in step 914. If it is determined that the process has entered the post-S3 IS phase 402, the generator 300 is powered "off" and set to the power level P0 in step 916. Then, it is determined in step 918 whether the power "off" duration is greater than a predetermined value, i.e., S3offDuration. The power "off" duration may start either immediately after the S3 high voltage pulse or instead may start after the post-S3 IS phase 402 has completed. After the power "off" duration reaches the S3offDuration, the process returns to step 902 in which the generator 300 is controlled to generate electrosurgical energy at the constant power level P1.

While several embodiments of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for controlling an electrosurgical generator, the method comprising:
generating electrosurgical energy during an impedance sense phase at an impedance sense power level for a first duration to sense an initial impedance of target tissue and, based on sensing the initial impedance, determining a tissue type of the target tissue;
continuously generating electrosurgical energy during a first phase at a first power level until a sensed impedance of the target tissue is greater than a first threshold impedance, the first threshold impedance being equal to a sum of the initial impedance of the target tissue and a predetermined impedance rise amount above the initial impedance of the target tissue, and in a case where electrosurgical energy is generated for an amount of time greater than a first phase limit, stopping generation of electrosurgical energy;
generating a first pulse of electrosurgical energy during a second phase at a second power level until the sensed impedance of the target tissue is greater than a second threshold impedance, the generating of the first pulse further including generating electrosurgical energy at the impedance sense power level for the first duration before and after the first pulse of electrosurgical energy to stabilize the sensed impedance of the target tissue;
generating a second pulse of electrosurgical energy during the second phase at the second power level until the sensed impedance of the target tissue is greater than a third threshold impedance;
generating electrosurgical energy at the impedance sense power level during a third phase to sense the impedance of the target tissue before generating at least one high voltage pulse;
generating at least one high-voltage pulse during the third phase at a third power level for a second duration to divide the target tissue; and
stopping the generation of the at least one high-voltage pulse during the third phase if a phase difference between voltage and current of the at least one high-voltage pulse is greater than a predetermined phase difference value, wherein:
the first power level is greater than the second power level, and the third power level is greater than the first power level,
in a case where the tissue type is determined to be low impedance tissue, the generating at least one high-voltage pulse includes generating a first predetermined amount of high-voltage pulses; and
in a case where the tissue type is determined to be high impedance tissue, the generating at least one high-voltage pulse includes generating a second predetermined amount of high-voltage pulses greater than the first predetermined amount of high-voltage pulses.

2. The method according to claim 1, wherein the second threshold impedance is equal to the sum of the initial impedance of the target tissue and an adjustable impedance rise amount above the initial impedance of the target tissue, wherein the third threshold impedance is greater than the second threshold impedance.

3. The method according to claim 2, wherein the adjustable impedance rise amount is multiplied by an adjustment factor for each successive pulse.

4. The method according to claim 1, further comprising generating, during the third phase, electrosurgical energy at the impedance sense power level to sense the impedance of the target tissue after generating the at least one high voltage pulse.

5. The method according to claim 1, wherein the pulses generated during the second phase are applied until the sensed impedance of the target tissue is greater than a maximum threshold impedance value.

6. The method according to claim 1, further comprising stopping the generation of at least one high-voltage pulse during the third phase if the sensed impedance of the target tissue exceeds a maximum threshold impedance value.

7. The method according to claim 1, wherein the generator is set to an off state having a fourth power level after each pulse of the plurality of pulses in the second phase for a predetermined duration, the predetermined duration being set such that the target tissue at least partially re-hydrates after each pulse of the plurality of pulses.

8. The method according to claim 1, wherein the generator is set to an off state having a fourth power level after each pulse of the at least one high-voltage pulse in the third phase for a predetermined duration, the predetermined duration being set such that the target tissue at least partially re-hydrates after each pulse.

9. The method according to claim 1, wherein the generator is set to an off state having a fourth power level after each pulse generated in first, second, and third phases, each off state having a predetermined duration.

10. The method according to claim 1, further comprising calculating a third threshold impedance based on determining that the sensed impedance of the target tissue is greater than the second threshold impedance,
wherein the third threshold impedance is equal to the second threshold impedance multiplied by a multiplication factor and the third threshold impedance is greater than the second threshold impedance.

11. A method for controlling an electrosurgical generator, the method comprising:
generating electrosurgical energy during an impedance sense phase at an impedance sense power level for a first duration to sense an initial impedance of target tissue;
generating electrosurgical energy during a first phase at a first power level until a sensed impedance of the target tissue is greater than a first threshold impedance, the first threshold impedance being equal to a sum of the initial impedance of the target tissue and a predetermined impedance rise amount above the initial impedance of the target tissue;
generating a first pulse of electrosurgical energy during a second phase at a second power level until the sensed impedance of the target tissue is greater than a second threshold impedance;
generating a second pulse of electrosurgical energy during the second phase at the second power level until the sensed impedance of the target tissue is greater than a third threshold impedance; and
generating at least one high-voltage pulse during a third phase at a third power level for a second duration to divide the target tissue,
wherein the third threshold impedance is less than the second threshold impedance.

12. An electrosurgical generator, comprising:
an RF output stage coupled to a power source, the RF output stage configured to generate electrosurgical energy from power provided by the power source for delivery to target tissue;
a sensor configured to sense an impedance of the target tissue; and
a controller configured to control the RF output stage to:
   generate electrosurgical energy during an impedance sense phase at an impedance sense power level for a first duration to sense an initial impedance of the target tissue and, based on sensing the initial impedance, determine a tissue type of the target tissue;
   continuously generate electrosurgical energy during a first phase at a first power level until a sensed impedance of the target tissue is greater than a first threshold impedance, the first threshold impedance being equal to a sum of the initial impedance of the target tissue and a predetermined impedance rise amount above the initial impedance of the target tissue measured by the sensor and, in a case where electrosurgical energy is generated for an amount of time greater than a first phase limit, stop generation of electrosurgical energy;
   generate a first pulse of electrosurgical energy during a second phase at a second power level until the sensed impedance of the target tissue is greater than a second threshold impedance, the generation of the first pulse further including generation of electrosurgical energy at the impedance sense power level for the first duration before and after the first pulse of electrosurgical energy to stabilize the sensed impedance of the target tissue,
   generate a second pulse of electrosurgical energy during a second phase at the second power level until the sensed impedance of the target tissue is greater than a third threshold impedance;
   generate electrosurgical energy at the impedance sense power level during a third phase to sense the impedance of the target tissue and to prepare the generator for a rapid rise in power to the third power level before generating at least one high voltage pulse;
   generate at least one high-voltage pulse during the third phase at a third power level for a second duration to divide the target tissue; and
   stop the generation of the at least one high-voltage pulse during the third phase if a phase difference between voltage and current of the at least one high-voltage pulse is greater than a predetermined phase difference value, wherein:
      the first power level is greater than the second power level, and the third power level is greater than the first power level,
      in a case where the tissue type is determined to be low impedance tissue, the generating at least one high-voltage pulse includes generating a first predetermined amount of high-voltage pulses; and
      in a case where the tissue type is determined to be high impedance tissue, the generating at least one high-voltage pulse includes generating a second predetermined amount of high-voltage pulses greater than the first predetermined amount of high-voltage pulses.

13. The electrosurgical generator according to claim 12, wherein the second threshold impedance is equal to an adjustable impedance rise amount above an initial impedance of the target tissue measured by the sensor,
wherein the third threshold impedance is greater than the second threshold impedance.

14. An electrosurgical generator, comprising:
an RF output stage coupled to a power source, the RF output stage configured to generate electrosurgical energy from power provided by the power source for delivery to target tissue;
a sensor configured to sense an impedance of the target tissue; and
a controller configured to control the RF output stage to:
   generate electrosurgical energy during an impedance sense phase at an impedance sense power level for a first duration to sense an initial impedance of the target tissue;
   generate electrosurgical energy during a first phase at a first power level until a sensed impedance of the target tissue is greater than a first threshold impedance, the first threshold impedance being equal to a sum of the initial impedance of the target tissue and a predetermined impedance rise amount above the initial impedance of the target tissue measured by the sensor;
   generate a first pulse of electrosurgical energy during a second phase at a second power level until the sensed impedance of the target tissue is greater than a second threshold impedance;
   generate a second pulse of electrosurgical energy during a second phase at the second power level until the sensed impedance of the target tissue is greater than a third threshold impedance; and
   generate at least one high-voltage pulse during a third phase at a third power level for a second duration to divide the target tissue,
wherein the third threshold impedance is less than the second threshold impedance.

* * * * *

UNITED STATES PATENT AND TRADEMARK OFFICE
CERTIFICATE OF CORRECTION

PATENT NO. : 10,285,750 B2
APPLICATION NO. : 14/255051
DATED : May 14, 2019
INVENTOR(S) : Coulson et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 300 days.

Signed and Sealed this
Thirty-first Day of December, 2019

Andrei Iancu
*Director of the United States Patent and Trademark Office*